United States Patent [19]

Webster

[11] Patent Number: 5,123,726
[45] Date of Patent: Jun. 23, 1992

[54] STEREOSCOPIC VIEWING SYSTEM AND METHOD

[75] Inventor: John A. Webster, Mt. Vernon, Wash.

[73] Assignee: Concept Vision Systems, Inc., Mt. Vernon, Wash.

[21] Appl. No.: 417,641

[22] Filed: Oct. 14, 1989

[51] Int. Cl.⁵ .......................... A61B 3/08; G02C 1/00
[52] U.S. Cl. .................................... 351/201; 351/158
[58] Field of Search ............... 351/201, 202, 158, 221; 350/130, 131, 133, 143, 145, 146; 362/103

[56] References Cited

U.S. PATENT DOCUMENTS

| | | |
|---|---|---|
| 3,166,395 | 1/1965 | Hicks, Jr. |
| 3,222,204 | 12/1965 | Weber et al. |
| 3,439,972 | 4/1969 | Ratliff, Jr. |
| 4,048,653 | 9/1977 | Spooner |
| 4,257,062 | 3/1981 | Meredith |
| 4,348,185 | 9/1982 | Breglia et al. |
| 4,632,508 | 12/1986 | Connelly |
| 4,709,263 | 11/1987 | Brumage |
| 4,714,320 | 12/1987 | Banbury |
| 4,732,160 | 2/1988 | Connelly |
| 4,740,836 | 4/1988 | Craig |
| 4,743,200 | 5/1988 | Welch et al. |
| 4,846,154 | 7/1989 | MacAnally et al. |
| 4,874,235 | 10/1989 | Webster ............................. 351/201 |

FOREIGN PATENT DOCUMENTS 1103961  4/1961  Fed. Rep. of Germany.

OTHER PUBLICATIONS

Meigs, "3-D TV Comes Home," *Popular Mechanics*, Aug. 1987, pp. 67-69, 88 and 90.

Primary Examiner—Rodney B. Bovernick
Attorney, Agent, or Firm—Christensén, O'Connor, Johnson & Kindness

[57] ABSTRACT

An apparatus and method for displaying and viewing full field-of-vision stereoscopic images is disclosed. The apparatus includes left and right display components including curved screens. The screens are suitable for mounting in a fixed position relative to the viewer's head and close to the viewer's eyes. The screens provide the normal single-eye full field of vision of 120° vertically and 180° horizontally. Each screen has a spherical central surface and a cylindrical temporal surface that extends from the central surface along the side of the viewer's head. The screens are mounted close to the viewer's eyes and optical components are provided to cause the viewer's eyes to be focused at the central surface. Contact lenses are suitable optical components. Contact lenses do not limit the viewer's field of vision and are continually oriented with the movements of the viewer's eyes.

9 Claims, 4 Drawing Sheets

STEREOSCOPIC VIEWING SYSTEM AND METHOD

GOVERNMENT RIGHTS

This invention was made with government support under Contract DAAH01-87-C-0817 awarded by the Defense Advanced Research Projects Agency. The government has certain rights in this invention.

This is a continuation-in-part of prior patent application Ser. No. 07/121,441, filed Nov. 17, 1987, now U.S. Pat. No. 4,874,235 the benefit of the filing date of which is hereby claimed under 35 U.S.C. § 120.

FIELD OF THE INVENTION

The present invention relates to an apparatus and method for viewing stereoscopic images. More particularly, the present invention uses contact lenses to adjust the relative focal point of the viewer to the central surface of a closely mounted curved screen that displays images across the full field of vision of the viewer.

BACKGROUND OF THE INVENTION

Three-dimensional viewing systems are rapidly developing, due to the vast areas in which such technology is useful. The duplication of normal visual perception has applications in the areas of: undersea (submersible) maintenance and search equipment; robotics; high-security surveillance; hazardous materials handling; entertainment; training simulator technologies; and education, to name a few. The goal of such systems is to substitute a computer-generated, recorded, or real-time remote reality for the user's current reality. Such systems may include audio, visual, and motion inputs to the user in order to create a total experience. The video aspect of such systems is known as stereoscopic viewing. Stereoscopy provides two views, i.e., a left and a right view, that are integrated by the viewer to give the impression of viewing three-dimensional objects.

The quality of stereoscopic systems depends largely on the field of vision presented to the viewer, clarity of the images, correctness of the colors and intensity of the images. A normal full field of vision for an adult can be defined by the area of visual attention coupled with the area of peripheral vision. The area of visual attention is that field in which the eye can maintain attention and sharp focus. For a single average eye this area spans about 120° vertically and horizontally in front of the eye. The area of peripheral vision extends from the area of attention along the temporal periphery and enhances the perception of the area of attention. For a single average eye, peripheral vision allows an additional 60° of vision along the horizontal plane. For purposes of this application, it will be assumed that an area spanning 120° vertically and 180° horizontally defines a full field of vision for an average adult single eye. The clarity, color, and intensity of the images displayed for viewing should be nearly equal to those of the real images that are being depicted.

Stereoscopic systems include three major components: image-gathering; image-processing; and presentation. For example, a conventional movie camera often serves as the image-gathering component. The image-processing component would then be the equipment and methods for retaining the images on film, i.e., film development. The presentation component could then be a movie screen and any viewer optical systems necessary for creating proper viewer perception. The present invention is related to a presentation component useful in a stereoscopic viewing system.

An example of a stereoscopic system is anaglyphic 3-D. The presentation component of an anaglyphic 3-D system consists of a screen and colored lenses worn by the viewer. The images displayed on the screen are left and right images that are projected through colored filters, i.e., a red and a blue filter, and superimposed on the screen. Conventionally, the colored lenses worn by the viewer coincide with the colored filters and thus separate the left and right views. The color-filtering lenses are mounted in eyeglass-type frames. In this manner, the left images are filtered into the left eye and the right images are filtered into the right eye, with all other images being blocked from view. Such a system suffers from the inability to achieve full and true image color, the reduction of image brightness, and the need for a true display system, i.e., clear screen display, to alleviate "ghosts" created by transient color surrounding the displayed images. Additionally, the field of vision in the described system is limited by the dimensions of the viewing glasses and the dimensions of the screen display.

A similar two-display system is the field sequential system. In such a system, the display, i.e., screen image, alternates between left and right images rather than superimposing them upon one another. The presentation component includes polarized, color-filtering, or piezoelectric glasses. The lenses are synchronized with the screen display. The synchronization causes the glasses to allow only left eye vision when the left image is displayed, and only right eye vision when the right image is displayed. Drawbacks in such a system include flickering of the images if a high number of frames per second is not achieved, loss of image intensity, and possible limited field of vision as a result of the use of eyeglasstype lenses and limited screen dimensions.

Certain stereoscopic viewing systems have replaced viewing glasses with special optics. One such system utilizes separate left and right LCD television screens mounted in a helmet in front of each eye. Wide-angle binocular optics are situated between the viewer and the screens. The optics are required to ensure that the left and right images properly overlap and are brought into focus. Image intensity is reduced in the optical system due to diffraction. Additionally, orientation of the viewer's eyes with the optics must be correct to avoid losing the images at the exit pupils and to avoid obstruction of the images by the lens frame.

Certain of the above-noted problems have been addressed in the area of recorded imaging. For example, the video industry has extended the display field of vision using multiple video screen displays, thereby increasing the illusion of reality by providing a wider field of vision. However, this particular solution may be inapplicable to real-time viewing because the uses for the stereoscopic technologies differ so widely. For example, a very small stereoscopic system is desirable for flight technology, i.e., an astronaut should be equipped with a helmet-mounted display rather than a large standard projection screen for viewing activities outside a space capsule.

As noted, in present stereoscopic viewing systems, images are generally dim because of the reduction in light intensity due to color and optical filtering; true color is difficult to achieve; full field of vision is not provided; and viewer orientation requirements are often restrictive. One result of these drawbacks is that an altered total visual reality is not achieved. Such a total visual reality would present images to a viewer, causing the viewer to accept those images as "real" and thus completely replacing the viewer's actual reality. An example of a total versus a partial alteration in reality can be illustrated using holographic 3-D. If a holographic image of a glass is projected on a table, then the viewer's actual reality is only partially altered, since the surrounding environment remains the same. However, if it were possible to holographically project new furniture and walls along with the glass, and all existing furniture and walls were masked, then the viewer's actual reality would be altered. Clues such as screen edges, dimness, color alterations, eyepiece edges, and orientation requirements all have a negative effect on a stereoscopic system's ability to create a total visual reality completely distinguishable from the viewer's actual reality. The present invention provides the means for creating total visual reality, while it overcomes the above-noted problems and others in the prior art.

SUMMARY OF THE INVENTION

An apparatus and method for displaying and viewing stereoscopic images is provided. In one embodiment, the apparatus includes a display component that is a part of an individualized viewing system. The images to be displayed are gathered and processed as left and right images that are differentiated on the display component. Curved left and right screens are used as the display component. The screens are positioned in close proximity to the viewer's eyes and alignment aids are included to maintain the screens in proper orientation with respect to the viewer's head. An optical component in the viewing system causes the image to be focused at the point at which the viewer's eyes will be positioned. The optical component may either cause focal length of the eyes of the viewer to be focused on the surface of the central portion of the screen, or cause the image to be focused at a short distance from the screen, i.e., at the position where the viewer's eyes will be oriented. Thus, while the viewer's eyes are relaxed, i.e., still focused in infinity, the screen images are clearly focused in the viewer's full range of vision. In accordance with the present invention, the optical component is a pair of frameless lenses that are always properly oriented with respect to the movement of the viewer's eyes. This prevents loss of images due to any exit pupil in the optical component and due to obstruction caused by the frames.

In accordance with still further aspects of the present invention, the apparatus includes a component for causing the screens to be securely mounted in close proximity to the viewer's eyes to maintain proper orientation of the screens with respect to the viewer's head.

In another embodiment of the optical component, left and right contact lenses are used to shorten the focal length of the viewer's eyes. The diopter is chosen for each lens in the pair, depending on the individual viewer's normal eyesight. Throughout the present application, it can be assumed that the viewer has perfect 20/20 vision. In that case, lenses of 30 diopters would focus the eyes at a point very close, i.e., within 1.31 inches, of the eye. In turn, the screen is mounted and dimensioned so as to be positioned at the focal point of the viewer's eyes. One skilled in the field of ophthalmology or optometry can determine the lens strength requirements for various natural vision characteristics coupled with the distance from the eye to the screen surface. Contact lenses, as the optical component, do not limit the viewer's normal field of vision. Thus, when a full field of vision is presented to the viewer by the display component, a full field of vision can be perceived. Contact lenses are also always correctly oriented in relation to the viewer's eyes.

In accordance with another aspect of the invention, the display component is made up of left and right screens that provide the full field of vision to the viewer. The full field of vision is defined by the area of visual attention and the area of peripheral vision. For purposes of this application, the full field of vision will be described by a 120° vertical and 180° horizontal area. The left and right screens are symmetrical about a horizontal axis extending forward from a point between the viewer's eyes. The left screen will be described, with the understanding that the right screen preferably has equal dimensions. The left screen is composed of central and temporal surfaces, which form a continuous screen. The central surface is spherical with a radius R. The central surface arcs 120° along the vertical plane, and 120° along the horizontal plane. The projected images obtained from an image-processor are aligned on the screen so that the projections are centered with the centerline of the viewer's vision. Thus, if the screen's center is slightly shifted from exact centerline of vision due to the viewer's head configuration, the center of projection is altered to provide clearly focused images at the viewer's centerline of vision.

The screen temporal surface is an extension of the central surface along the temporal side of the device in relation to the viewer. The surface is curved with a similar radius R. The side surface tapers to a point along the side of the head so that a 180° horizontal arc is formed by the screen between the inner nasal edge of the central surface and the outermost point of the temporal surface. Thus, the normal full field of vision, estimated as 180° horizontal and 120° vertical, is provided to each eye.

In accordance with still further aspects of the present invention, the image display component includes left and right corrective surfaces for causing the viewer's eyes to be relatively normally focused on images viewed therethrough. The corrective surfaces extend from the left and right image display surfaces, e.g., downwardly therefrom, such that the corrective surfaces and the image display surfaces form left and right viewing surfaces, respectively, that span the full field of visual attention and peripheral vision of the viewer.

In accordance with still another aspect of this invention, two methods can be used to determine a suitable radius for the screen surfaces. The first is described above, wherein a reasonably strong diopter is chosen and the focal length of a person wearing a contact lens with that strength is calculated. The radius of the screen is then equal to the calculated focal length. The diopter must be chosen to provide a short enough focal length, and thus radius, so that the screens do not physically or optically interfere with one another. Alternatively, the radius of the screen is chosen to be slightly less than one-half of the viewer's interpupillary distance. The contact lens diopter is then determined so that the focal length equals the radius. The latter method provides left and right screens that comfortably fit on the viewer's face without physically or optically interfering with one another. The radius is also adjusted for other facial characteristics, such as nose size, etc.

In accordance with further aspects of this invention, the screens are formed from optic fibers. The optic fibers are coherently bundled. One end of the optic fiber bundle is connected to a device, such as a CRT, used to transmit images. At the opposite end, the fiber ends are cut and polished to provide a concave screen configuration that provides the full field of vision to the viewer. In this manner, flat displays such as those transmitted by the CRT, are transformed into curved displays. The optic fiber ends are polished by smooth grinding and are coated with a single layer of glass microbeads. A viscous coating is sprayed over the fiber end surface and the glass microbeads are applied to the coating. The coating has a viscosity that is related to the diameter of the microbeads to prevent capillary attraction between the microbeads. Thus, when the coating has dried, the excess microbeads are removed and a single layer of microbeads remains on the surfaces. The microbeads act to diffuse the light exiting the optic fiber surfaces so that light that would have otherwise exited at an angle away from the viewer's vision is directed toward the centerline of vision.

As will be readily appreciated from the foregoing description, the invention provides the presentation component for a stereoscopic viewing system. The invention includes a display and an optical component. The full field of vision is available to the user because the optical component does not limit the viewer's natural eye movements, and does not have a frame edge or exit pupil. Thus, when coupled with the curved screen that displays an image spanning the viewer's full range of view, a total visual reality is achieved. By securely positioning the screen in proper orientation adjacent the viewer's eyes, the displayed images are presented to the viewer without disruption caused by movement of the viewer's head. Additionally, the methods for dimensioning the screens ensures that the left and right image displays do not optically interfere with one another, as well as ensuring that the display components do not physically interfere with one another. The brightness of the images obtained from the image processor is maintained by the screen surface and the optical component, and image colors are retained, since the optical component does not require color filtering to differentiate between left and right images.

BRIEF DESCRIPTION OF THE DRAWINGS

The foregoing and other advantages and features of this invention will become more readily appreciated as the same becomes better understood by reference to the following detailed description when taken in conjunction with the accompanying drawings, wherein.

DETAILED DESCRIPTION OF THE PREFERRED EMBODIMENT

Figure 1:
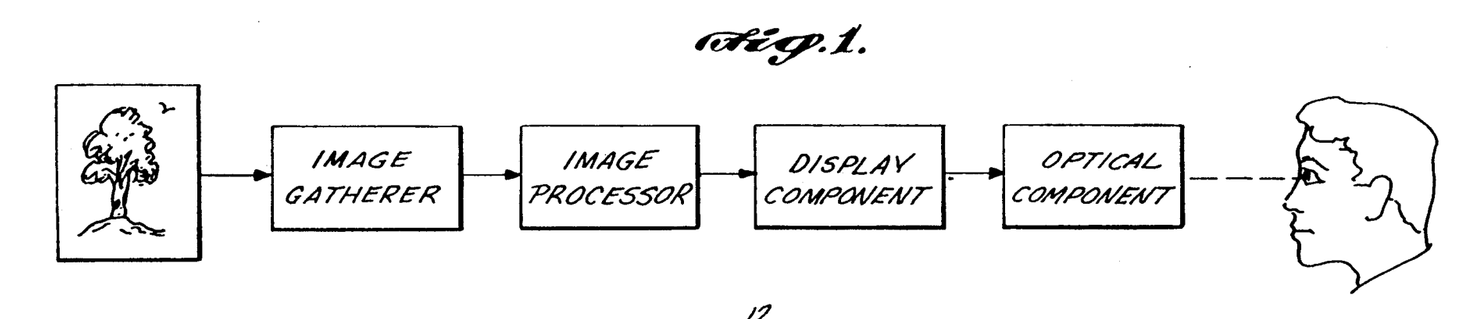
FIG. 1 is a block diagram of a steroscopic viewing system of which the present invention is a component.

The components of a stereoscopic imaging system are illustrated in FIG. 1. Left and right images are gathered by the image gatherer using left and right cameras mounted at a set distance apart. The left and right images are processed by an image processor. The images are then displayed in a manner that continues to differentiate between the left and right images. An optical component is positioned between the display component and the viewer to properly focus the displays. The display and optical components of the present invention have left and right sides to be used in conjunction with the left and right eyes of the viewer.

Figure 2:
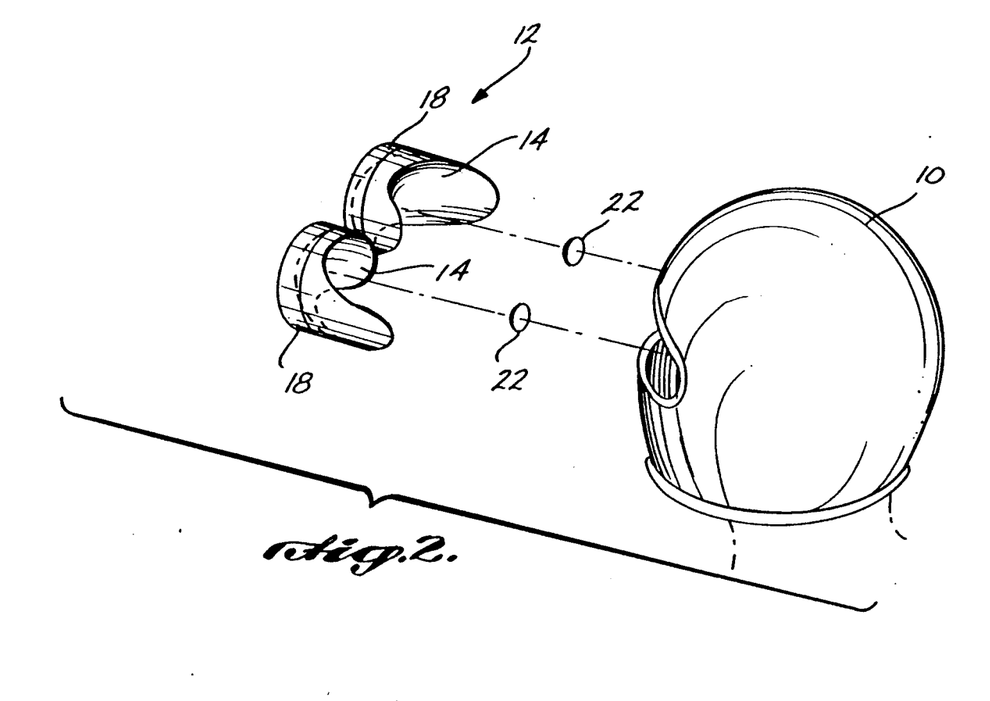
FIG. 2 is an exploded pictorial view of a stereoscopic viewing system in which the present invention is a component.

FIG. 2 illustrates one preferred embodiment of the display and optical components in a stereoscopic system. Single reference numbers will be used throughout the present description to identify equivalent left and right components. It is to be understood that subreferences (a) and (b) refer to left and right components, respectively. The stereoscopic system is integrated into helmet 10. The display component 12 is securely mounted within the helmet. The display component 12 includes screens 14. Screens 14 are thus positioned in close proximity to the viewer's eyes when the helmet is worn. The display component 12 receives image information from an image processor (not shown) at interfaces 18. The optical component is a pair of contact lenses 22 to be worn by the viewer. The helmet 10 aids in blocking external indications of actual reality from viewer perception and in maintaining the relative orientation of the screens with respect to the viewer's head. Other devices for carrying out these functions could be used.

Figure 3:
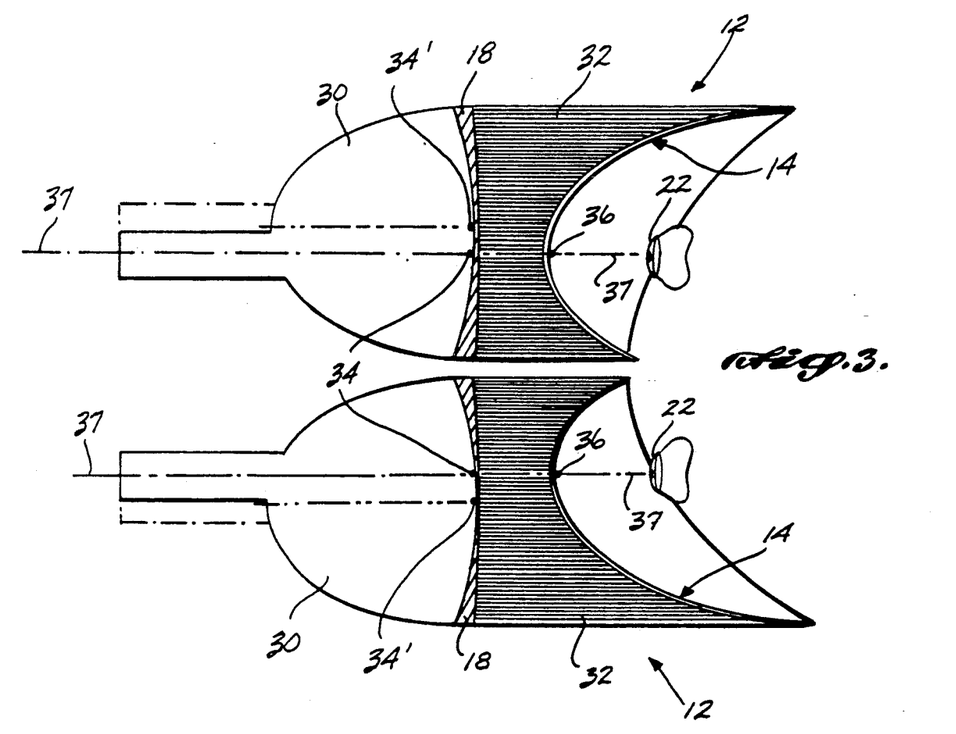
FIG. 3 is a schematic cross-sectional view along a horizontal line of the display and viewing components of one preferred embodiment of the present invention.

FIG. 3 shows the display and optical components of a preferred embodiment of the invention in a schematic view of a horizontal cross section of the components. The display component 12 is made up of optic fiber bundles 32 and screens 14. The optical component is contact lenses 22.

A pair of video display fiber-optic-face CRTs 30 interface with the optic fiber bundles 32 at interfaces 18. The flat images carried by the CRTs 30 are thus transferred to the optic fiber bundles 32 at interfaces 18. The optic fibers 32 terminate opposite interfaces 18 in screens 14.

The CRTs' centerlines 34 and the screens' centerlines 36 are aligned with the centerlines of vision 37, which are defined by known characteristics of the human eye. The centering of the CRTs' centerlines 34 is preferably done by mechanically offsetting the video display CRT inputs as shown. An alternative embodiment utilizes symmetrical CRT inputs shown in reference with centerlines 34'. In the alternative embodiment, the images at interfaces 18 are electronically adjusted in order to align the image centers with the screens' centerlines 36.

The surfaces of screens 14 are preferably formed by smooth grinding of the optic fiber ends. The optic fiber ends are then coated with a single layer of glass microbeads (not shown). The glass microbead layer is applied by coating the fiber ends with a highly viscous coating, spraying the glass microbeads onto the coating, and blowing off the excess beads so as to leave a single layer of beads clinging to the optic fiber ends. The diameter of the microbeads dictates the resolution that will be viewed through the microbeads. Additionally, the wavelength of light transmitted through the screens is controlled by the wavelength of the microbeads.

One suitable viscous coating is an ultraviolet setting optical epoxy. The epoxy is thinned to a consistency such that the epoxy is sprayable and will create a self-leveling glue layer across the fiber ends. Once the epoxy is applied, the thinner is allowed to evaporate from the glue layer. After the thinner has evaporated, the microbeads are sprayed onto the epoxy in a thickness, e.g., several microbeads thick, adequate to ensure that the epoxy is completely covered. The epoxy is then hardened. The hardening process is carried out by subjecting the epoxy to intense ultraviolet light. After the epoxy is completely hardened, the excess microbeads are shaken loose from the surface and removed by blowing them off of the surface. The single layer of microbeads remaining forms the screen surface.

The viscous coating preferably has no capillary attraction with the microbeads in order to prevent more than a single layer of the glass microbeads from adhering to the fiber ends. Capillary attraction of the microbeads during the screen manufacturing process is avoided by controlling the viscosity of the epoxy in relation to the diameter of the microbeads. The viscosity is preferably inversely proportional to the diameter of the microbeads. For example, in one actual embodiment, the microbead diameter is less than or equal to 7 microns. A suitable epoxy for use with these microbeads is Norland Optical Adhesive No. 68, available from Norland Products, Inc., of New Brunswick, N.J.

Figure 4:
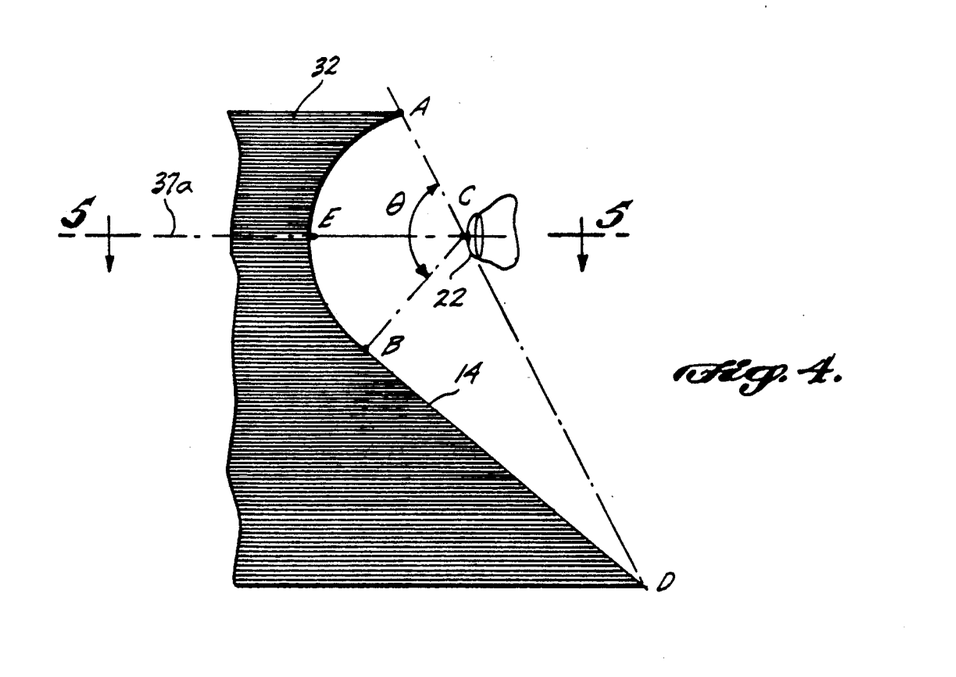
FIG. 4 is a horizontal cross-sectional view of the display component in accordance with the present invention, with the cross-sectional plane including the centerline of vision.
Figure 5:
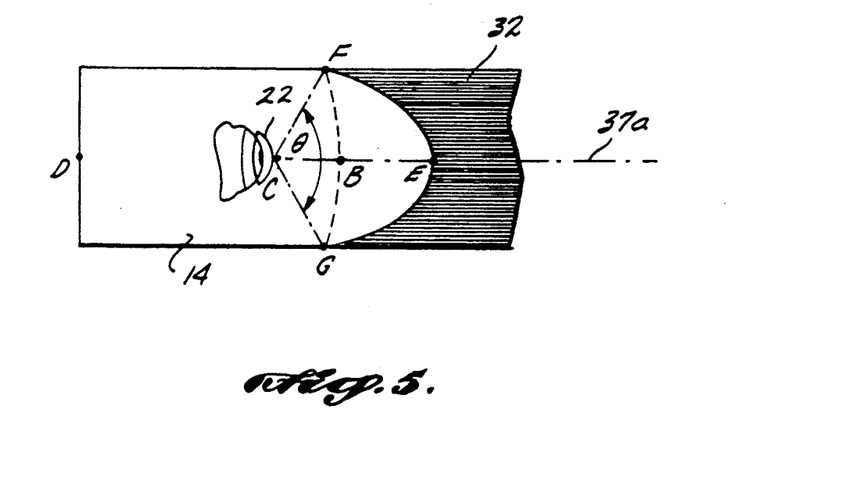
FIG. 5 is a side elevational view of a cross section of the display component in accordance with the present invention, with the cross-sectional plane including the centerline of vision.

The geometry of the screens 14 is illustrated in FGIS. 4 and 5. The below-described dimensions of the lenses provide a viewer with an interpupillary distance of about 2.37 inches, with the full field of vision as gathered by the image-gathering component. The dimensions of one preferred embodiment of the screens will be described in terms of left screen 14(a). It is to be understood that right screen 14(b) is similarly dimensioned.

FIG. 4 is a cross-sectional top view of the left screen 14(a), cut along a horizontal plane including centerline of vision 37(a). The central surface of the screen between points A and B is spherical with a radius of 1.31 inches. The angle θ formed between lines AC and CB is 120°. In the preferred embodiment, line EC bisects angle ACB. Line BD is a straight line. It represents a line bisecting the length of the cylindrical temporal surface with a similar radius of 1.31 inches. The temporal surface of the screen terminates at D. The angle formed by lines AC and CD is 180°. Thus, the full horizontal field of vision is provided to the viewer.

FIG. 5 is a cross-sectional side view of the left screen 14(a), cut along a vertical plane including centerline of vision 37(a). The cross section of the screen between F and G is spherical with a radius of 1.31 inches. FG is the line of intersection of the central surface and the temporal surface of screen 14(a). The angle θ formed by lines FC and CG is 120°, 60° above and below the centerline of vision 37(a). Thus, screen 14(a) provides the full 120° vertical field of vision to the viewer. The side surface extends temporally with a constant radius of 1.31 inches, from FG to terminate at D.

For the viewer with an interpupillary distance of about 2.37 inches, screens 14 with radii of 1.31 inches can be mounted side by side and in front of the viewer's eyes without interfering with one another or with the viewer's nose. The interpupillary distance for the average American adult is 2.36 to 2.71 inches. Thus, screens for the average person would have radii between 1.1 and 1.3 inches. It is to be understood that the radii of the screens can vary beyond this average range, depending on facial characteristics such as nose size and interpupillary distance.

The optical lenses 22 for use in conjunction with the screens 14 are single contact lenses. The lenses are of adequate strength to adjust the viewer's natural focal length to equal the radius of the central curved surface. This correction to the natural focal length is accomplished by using a converging lens which, in effect, moves the projected images farther from the eyes to a point where a sharp retinal image can be formed. For a person with normal eyesight, i.e., 20/20 vision, for a screen with radius equal to 1.31 inches, a lens of 30 diopters would be appropriate. Such a correction will bring the screen into focus, while the viewer's eyes remain relaxed and focused at infinity. Methods for determining the proper lens strength and for manufacturing such lenses are known.

Figure 6:
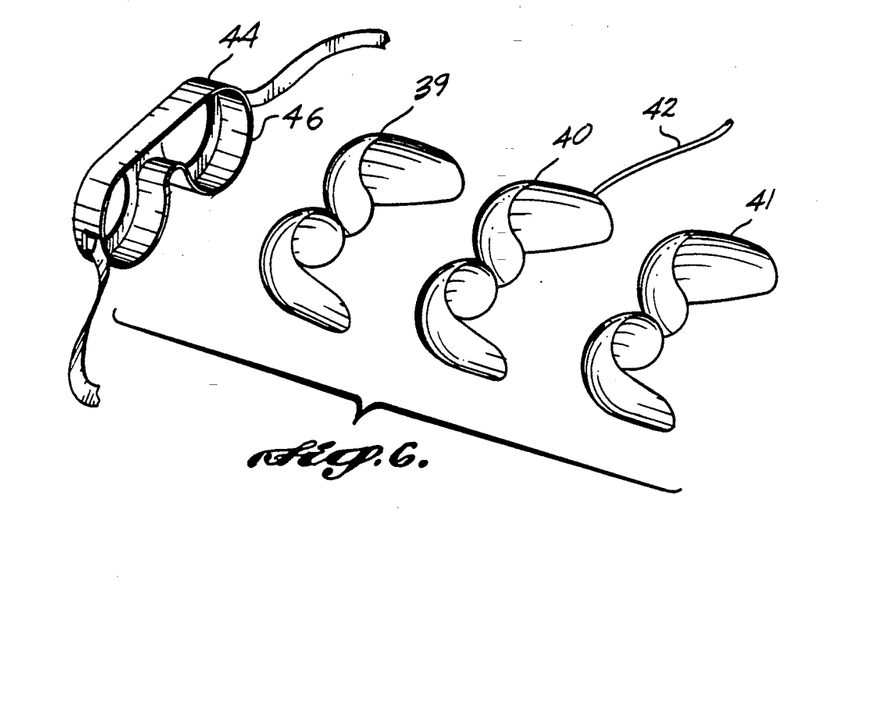
FIG. 6 is an exploded pictorial view of a display component in accordance with the present invention.

With reference to FIG. 6, in an alternative preferred embodiment, the viewing system includes a backing layer 39, an imaging layer 40, a screen 41, and an image receiving component 42. Each layer includes a left and right side. The dimensions of the backing layer 39, the imaging layer 40 and screen layer 41 are similar to the dimensions of screen 14 described above. Each of these layers is relatively thin. Thus, the viewing system as a whole is relatively light weight. The series of layers is supportable in a helmet similar to helmet 10 described above. Alternatively, the layers are encased in goggles 44 and strapped to the head.

The backing layer 39 is made of a rigid material such as glass and is used to support the imaging layer. The imaging layer 40 is preferably a light emitting diode (LED) display, liquid crystal display (LCD), or thin film image display layer. The imaging layer receives left and right image signals from the image processor (not shown) through the image receiving component 42 which is a signal carrying device. The screen 41 is an optic fiber layer coated with glass microbeads as described above. The optic fibers are aligned perpendicularly to a plane tangent to the inside viewing surface of the screen.

In one preferred embodiment, the layers are secured within goggles 44. The edge 46 of the goggles is shaped so as to conform to an average viewer's face near the eyes. The edge 44 acts to properly align the screen centers with the viewer's centerline of vision. Additionally, the goggles act to block out all aspects of actual reality so that the viewer's total visual reality is formed by the screen images. In use, the viewer utilizes an optical component such as contact lenses 22 to cause the image on the screens to be closely focused when the helmet or goggles are worn.

Figure 7:
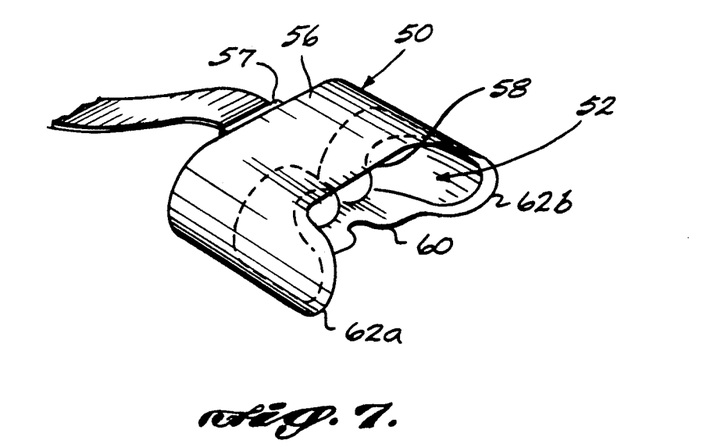
FIG. 7 is a pictorial view of a stereoscopic viewing system in accordance with the present invention.

With reference to FIG. 7, an alternative preferred embodiment includes a tubular viewing system 50. The viewing system includes an image display component 52 that is similar to display component 12 or screen 41. The imaging system also includes an imaging device such as the CRTs 30 or the imaging layer 40. A suitable interface, such as optic fibers, between the imaging device and the display component screens is provided. A tube 56 encases the screens, the imaging device, and the interface. At the end of the tube opposite the screens an image receiving component 57 is connected. Left and right images are thus received from an image processor (not shown) and transmitted to the display component.

The front portion of the tube 56 containing the screens includes a forehead brace 58, a lower brace 60, and left and right temporal extensions 62a and 62b, respectively. Preferably, the edge portions of the tube including the braces and extensions are made from a semipliable or padded material. The forehead brace 58 is shaped so as to conform to an average adult forehead. The lower brace 60 is shaped to conform to the cheekbones and nose of an average adult. The temporal extensions extend along and beyond the temporal surface of the screens. To utilize the viewing system, a viewer positions his/her face against the braces and between the extensions. The contours of the tube edge act as references for the viewer to properly align the centerline of the screen with the viewer's centerlines of vision. The padding on the braces and extensions allows the viewer to exert pressure against the tube 56. The pressure causes the tube edges to conform to the viewer's face thereby elimating all tube edges from sight. In this manner, the viewer's total visual reality is altered since only the images on the screens 52 are perceived by the viewer.

In the tubular viewing system, the optical component includes contact lenses such as lenses 22 described above and a counter-corrective device such as conventional eyeglasses (not shown). The correction of the eyeglass lenses negates the effects of the contact lenses. Thus, stereoscopic and normal viewing are both readily achievable. When the viewer is remote from the tube, the corrective eyeglasses are worn so that relatively normal vision is achieved. The eyeglasses are removed during the stereoscopic viewing session.

Figure 8:
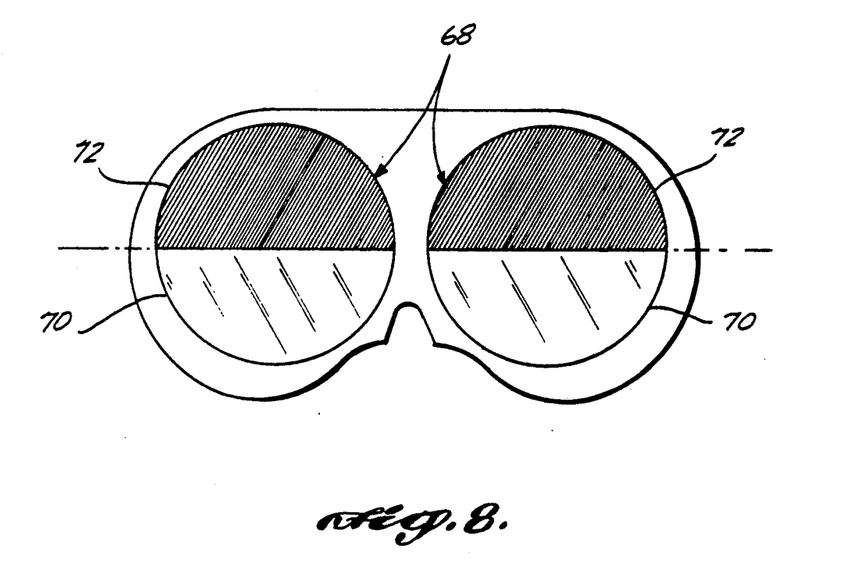
FIG. 8 is a rear elevation view of viewing screens in accordance with the present invention.

With reference to FIG. 8, a flight simulator type of imaging system incorporates a display component with screen 68 having corrective portion 70 and stereoscopic portion 72. Such a display component could be integrated into a device such as helmet 10. The majority of the display component is similar to display component 12 with the exception of the screen. The screen 68 includes corrective portion 70 that is made of corrective lenses that negate the correction of the optical components such as contact lenses 22. The stereoscopic portion 72 is similar to screen 14 and is in the upper portion of the screen 68. Thus, when the helmet is worn, the viewer may view the surrounding actual reality by looking downwardly through the corrective portion 70 of the screen, and view the displayed stereoscopic image by looking up at the stereoscopic portion 72 of the screen. An example of the use of such a display system is in flight simulation. The viewer would view the various flight instrument panels through the lower portion of the screen and would view a flight simulation through the upper portion.

While preferred embodiments of the invention have been illustrated and described, it will be appreciated that various changes can be made therein without departing from the spirit and scope of the invention. For example, curved screen systems other than fiber-optic screens could be used. A fiber-optic screen without the glass microbead coating could be used if the optic fibers are of a high enough numerical aperture to cause the light being transmitted to diffuse normally toward the eye. Additionally, screens of different dimensions, i.e., a single closely mounted wraparound screen, could be used if a means, e.g., colored contact lenses, were used to distinguish left and right images. Alternative optical components may also be used. For example, a series of curved holographically etched focusing and collimating layers may be included adjacent the display component, i.e., between the display component and the viewer. These layers are layers of thin film that contain a hologram of an optical element or series of optical elements. The holographic optical element has a focal length equal to the internal radius of the screen as measured from the viewing point to the imaging surface. Thus, the holographic optical element will cause the displayed images to be focused at the viewer's closely positioned focal point. Holographic optical elements typically generate a high amount of diffraction. Therefore, a layer of color correcting material is included between the holographic layers and the viewer. Finally, the correction provided by the contact lenses should be specific for each user of the system. Thus, if the user is naturally farsighted, the lens will compensate for that characteristic, while still providing for the proper focal point in relation to the positioning of the screens.

An alternative method for generating the image is to utilize horizontally run film having pairs of left and right frame images. For example, 70 mm movie film could produce an extremely high resolution image. The film is shot with a single dual-lensed camera that exposes left and right images on alternating frames at the same time. The image frames on the film are thus left and right image pairs. The film is viewed by running it by and in contact with the flat ends of the fiber-optic bundles, two frames at a time. The light source is either shuttered or strobed to ensure that the proper scene is viewed by each eye.

The embodiments of the invention in which an exclusive property or privilege is claimed are defined as follows:

1. Apparatus for the viewing of stereoscopic images by a viewer, the apparatus being used in conjunction with contact lenses that cause the viewer's eyes to be closely focused, comprising:

image display means including means for receiving signals representative of separate left and right images, left and right concave display surfaces, each surface having a display center, and means for displaying said left and right images on said display surfaces; and mounting means for aligning said display surfaces relative to the viewer's head such that the viewer's centerlines of vision are aligned with said display centers, whereby the viewer's eyes are focused on said display surfaces.

2. The apparatus for the viewing of stereoscopic images as claimed in claim 1, wherein said left and right display surfaces each include a central surface, a temporal surface and a temporal edge, said central surface being spherical with radius R, spanning the full field of visual attention, and including said display center, and said temporal surface being a continuous cylindrical extension of said central surface toward said temporal edge of said display surface, having radius R, and spanning the full field of peripheral vision.

3. The apparatus for the viewing of stereoscopic images as claimed in claim 2, wherein said radius R is less than or equal to one-half the interpupillary distance of the viewer.

4. The apparatus for the viewing of stereoscopic images as claimed in claim 2, wherein said image display means is comprised of optic fibers.

5. The apparatus for the viewing of stereoscopic images as claimed in claim 4, wherein said left and right display surfaces are optic fiber ends coated with a single layer of glass microbeads.

6. The apparatus for the viewing of stereoscopic images as claimed in claim 1, wherein said image display means further includes left and right corrective surfaces for causing the viewer's eyes to be relatively normally focused on images viewed therethrough, said corrective surfaces extending from said left and right image display surfaces such that said left and right corrective surfaces and said left and right image display surfaces form left and right viewing surfaces, respectively, whereby said left and right viewing surfaces span the full field of visual attention and peripheral vision of the viewer.

7. The apparatus for the viewing of stereoscopic images as claimed in claim 6, wherein said left and right corrective surfaces extend downwardly from said left and right image display surfaces, respectively, such that said corrective surfaces form the lower portions of said viewing surfaces.

8. Apparatus for the viewing of stereoscopic images by a viewer, comprising:

image display means including means for receiving signals representative of left and right images, left and right concave display surfaces, each surface having a display center, and means for displaying said left and right images on said display surfaces;

mounting means for aligning said image display means relative to the viewer's head such that the viewer's centerlines of vision are aligned with said display centers; and nonobstructive optical means for focusing the viewer's eyes at said display surfaces.

9. The apparatus for the viewing of stereoscopic images as claimed in claim 8, wherein said optical means is a pair of contact lenses.

* * * * *

UNITED STATES PATENT AND TRADEMARK OFFICE
CERTIFICATE OF CORRECTION

PATENT NO. : 5,123,726
DATED : June 23, 1992
INVENTOR(S) : John A. Webster

It is certified that error appears in the above-identified patent and that said Letters Patent is hereby corrected as shown below:

| COLUMN | LINE | |
|---|---|---|
| 2 | 37 | "eyeglasstype" should read --eyeglass-type-- |
| 7 | 36 | "FGIS." should read --FIGURES-- |
| 9 | 24 | "elimating" should read --eliminating-- |
| [56] | 10th Ref. | "4,732,160" 2/1988 Connelly" should read --4,723,160 2/1988 Connelly-- |

Signed and Sealed this

Twenty-first Day of December, 1993

Attest:

BRUCE LEHMAN

Attesting Officer  Commissioner of Patents and Trademarks